United States Patent [19]

Gallo et al.

[11] Patent Number: 4,520,113

[45] Date of Patent: May 28, 1985

[54] SEROLOGICAL DETECTION OF ANTIBODIES TO HTLV-III IN SERA OF PATIENTS WITH AIDS AND PRE-AIDS CONDITIONS

[75] Inventors: Robert C. Gallo; Mikulas Popovic, both of Bethesda, Md.; Mangalasseril G. Sarngadharan, Vienna, Va.

[73] Assignee: The United States of America as represented by the Secretary of the Department of Health and Human Services, Washington, D.C.

[21] Appl. No.: 602,945

[22] Filed: Apr. 23, 1984

[51] Int. Cl.$^3$ .................... G01N 33/54; G01N 33/56
[52] U.S. Cl. .................................. 436/504; 436/510; 436/515; 436/530; 436/531; 436/543; 436/804; 436/808; 436/809; 436/811; 436/546; 435/5; 435/7; 435/194; 435/239; 435/810; 435/948; 422/61; 424/86; 424/89
[58] Field of Search ............... 436/536, 542, 800, 804, 436/807–809, 813, 504, 510, 514, 515, 530, 531, 543, 811, 546; 435/7, 235–240, 259–261, 810, 948, 4, 5, 194; 424/1.1, 89, 93, 86; 422/61

[56] References Cited

PUBLICATIONS

Robert-Guroff, M. et al., Science, vol. 215, pp. 975–978, (2-1982).
Essex, M. et al., Science, vol. 220, pp. 859–862, (5-1983).
Gallo, R. C. et al., Science, vol. 220, pp. 865–867, (5-1983).
Barre-Sinoussi, F. et al., Science, vol. 220, pp. 868–871, (5-1983).
J. National Cancer Institute, vol. 69(4), pp. 981–985, (10-1982), Essex, M.
Posner, L. E. et al., J. Experimental Medicine, vol. 154, pp. 333–346, (8-1981).
Hinuma, Y. et al., Proc. Natl. Acad. Sci. USA, vol. 78(10), pp. 6476–6480, (10-1981).
Kalyanaraman, V. S. et al., Nature, vol. 294, pp. 271–273, (11-1981).
Marx, J. L., Science, vol. 224, pp. 475–477, (5-1984). (Not Prior Art).
Sarngadharan, M. G. et al., Science, vol. 224, pp. 506–508, (5-1984). (Not Prior Art).
Schupbach, J. et al., Science, vol. 224, pp. 503–505, (5-1984). (Not Prior Art).
Gallo, R. C. et al., Science, vol. 224, pp. 500–503, (5-1984). (Not Prior Art).
Popovic, M. et al., Science, vol. 224, pp. 497–500, (5-1984). (Not Prior Art).
Jaffe, H. W. et al., Science, vol. 223(4642), pp. 1309–1312, (3-1984).
Mitsuya, H. et al., Science, vol. 223(4642), pp. 1293–1296, (3-1984).
Leavitt, R. D., Eur. J. Clin. Microbiol., vol. 3(1), pp. 79–84, (2-1984).
Kalyanaraman, V. S. et al., Virology, vol. 132, pp. 61–70, (1984).
Kreise, J. K. et al., Annals Int. Medicine, vol. 100, pp. 178–182, (1984).

(List continued on next page.)

*Primary Examiner*—Ben R. Padgett
*Assistant Examiner*—M. Moskowitz
*Attorney, Agent, or Firm*—John S. Roberts, Jr.

[57] ABSTRACT

This invention relates to the detection of antibodies in sera of AIDS and pre-AIDS patients and describes the biochemical and immunological analysis of antigens associated with the virus HTLV-III Human T-Cell Leukemia Virus. It is shown that antigens associated with the infection of human cells by this virus are specifically recognized by antibodies from AIDS patients. Specifically, HTLV-III isolated from AIDS patients and transmitted by cocultivation with an HT cell line is specifically detected by antibodies from human sera taken from AIDS patients. The method of detection of antibodies preferred is a strip radioimmunoassay (RIA) based on the Western Blot technique or an ELISA (an enzyme-linked immunosorbent assay) or an indirect immunofluorescence assay.

10 Claims, 1 Drawing Figure

PUBLICATIONS

Brun-Vezinet, F. et al., The Lancet, I, pp. 1253-1256, (6-1984). (Not Prior Art).

Kalyanaraman, V. S. et al., Science, vol. 225, pp. 321-323, (7-1984). (Not Prior Art).

Tsang, V. C. W. et al., Methods in Enzymology, vol. 92, pp. 377-391, (1983).

Saxinger, C. et al., Laboratory Investigation, vol. 49(3), pp. 371-377, (1983).

de Thé, G. et al., C. R. Acad. Sc. Paris III, vol. 297(4), pp. 195-197, (10-1983).

Evatt, B. L. et al., The Lancet, vol. 2(8352), pp. 698-700, (1983).

Essex, M. et al., Science, vol. 221(4615), pp. 1061-1064, (9-1983).

Gelmann, et al., *Science,* 220:862-865, May 20, 1983.

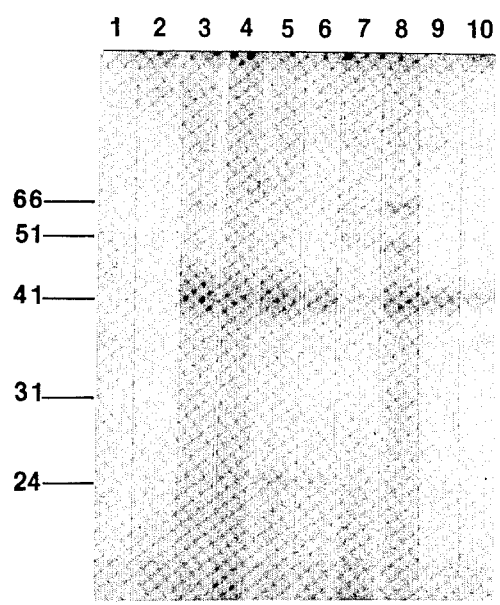

SEROLOGICAL DETECTION OF ANTIBODIES TO HTLV-III IN SERA OF PATIENTS WITH AIDS AND PRE-AIDS CONDITIONS

This invention relates to the detection of antibodies in sera of AIDS and pre-AIDS (Acquired Immune Deficiency Syndrome) patients and describes the biochemical and immunological analysis of antigens associated with the virus HTLV-III. It is shown that antigens associated with the infection of human cells by this virus are specifically recognized by antibodies from AIDS patients. Specifically, HTLV-III isolated from AIDS patients and transmitted by cocultivation with an HT cell line is specifically detected by antibodies from human sera taken from AIDS patients. The detection method preferred is a strip radioimmunoassay (RIA) based on the Western Blot technique and ELISA (an enzyme-linked immunosorbent assay).

STATEMENT OF DEPOSIT

A cell line corresponding to the present invention, and denoted H9/HTVL-III$_B$, has been deposited in the American Type Culture Collection, 12301 Parklawn Dr., Rockville, MD 20852 (under ATCC No. CRL 8543) on Apr. 19, 1984, prior to the filing of this patent application. This deposit assures permanence of the deposit and ready accessibility thereto by the public. H9 is a representative and preferred cloned cell line in accordance with the invention.

DESCRIPTION OF THE FIGURE

FIG. 1 illustrates identification of HTLV-III antigens recognized by sera of AIDS patients.

BACKGROUND OF THE INVENTION

A family of T-lymphotropic retroviruses causes T-cell proliferation leukemia, T-cell depletion, and immunosuppression in humans infected by the viruses. These retroviruses are known as the HTLV family of T4 tropic retroviruses. Subgroup HTLV-I causes T-cell proliferation in leukemia; subgroup HTLV-II induces T-cell proliferation in vitro but its role in disease is unclear. A third group of related virus, collectively designated HTLV-III, has now been isolated from cultured cells of patients with acquired immune deficiency syndrome (AIDS). The biological properties of HTLV-III and immunological analysis of its proteins show that this virus is a member of the HTLV family and closely related to HTLV-II. Sera of 88% of patients with AIDS and of 79% of homosexual men with pre-AIDS, but less than 1% of heterosexual donors have antibodies reactive against antigens of HTLV-III. The major immune reactivity appears to be directed against p41, a 41,000 m.w. protein, believed to be an envelope antigen of the virus.

Acquired immune deficiency syndrome (AIDS) is a relatively recently recognized disease evident in several parts of the world. Its overwhelming prevalence among homosexual men with multiple sexual partners, illegal intravenous drug abusers, hemophiliacs, blood transfusion recipients, and close heterosexual contacts of members of the above high-risk groups strongly suggests that the disease spreads by the transmission of an infectious agent. The primary targets of affliction in the human body are specific subpopulations of T-cells. The severe immune deficiency of these patients results from an unusually low proportion of helper T-cells (T4) in their lymphocyte population, thus reducing the availability of many T4 helper functions, among which is the production of antibodies by B-cells.

Retrovirus infection is known to lead to depressed immune functions in animal systems. Analogizing the human response to these non-animal systems, a human retrovirus with a tropism for T-cells was considered a candidate in the etiology of human AIDS. As mentioned above, several members of a family of human T-lymphotropic retroviruses (HTLV) have been isolated. One of these isolates was obtained from a black American with an aggressive form of T-cell lymphoma. This virus, designated HTLV-I, has been etiologically linked to the pathogenesis adult T-cell leukemia/lymphoma (ATLL). In vitro infection with HTLV-I can alter T-cell function and, in some cases, leads to T-cell death. Another member of the HTLV family was isolated from a patient with a T-cell variant of hairy cell leukemia and was designated HTLV-II. Isolation of HTLV-I and HTLV-II have been reported from cultured T-cells of patients with AIDS. Isolation of another retrovirus was reported from a homosexual patient with chronic generalized lymphadenopathy, a syndrome that often precedes AIDS and therefore referred to as "pre-AIDS." Proviral DNA of HTLV-I was detected in the cellular DNA of two AIDS patients, and sera of some patients were shown to react with antigens of HTLV-I. The correlation between AIDS and serum antibodies to HTLV-I protein is weak. The present invention shows that the primary cause of the syndrome is a human T-lymphotropic retrovirus variant with limited cross reactivities with the known HTLV-subgroups. These new variants are designated HTLV-III and are the subject of the present invention. Disclosed is the use of this virus in an immunological screening of sera of patients with AIDS, pre-AIDS, and individuals at increased risk for AIDS.

HTLV-III was purified from supernatants of cell cultures supporting the continuous production of these cytopathic viruses. These HTLV variants (HTLV-III) lack immortalizing (transforming) properties for normal T-cells and mainly exhibit cytopathic effects on the T-cell helper. The cytopathic effect was overcome by finding a highly susceptible, permissive cell for cytopathic variants of HTLV, thus preserving the capacity for permanent growth after infection with the virus. These cell cultures allow for the continuous production of the HTLV-III virus. Cell line HT is infected with HTLV-III virus in order to obtain a reproducible source of the virus. Antigens associated with the virus obtained from these cultures are reacted with human sera from suspected AIDS patients. Assays by the Western Blot technique and ELISA technique determine whether the patient examines positive for AIDS.

GENERAL DESCRIPTION

Incorporated by reference is a copending application of the same inventorship entitled, "Method of Continuous Production of Retroviruses (HTLV-III) from Patients with AIDS and pre-AIDS, Ser. No. 602,946."

Lysates of immortalized human T-cell clones, H9, to which HTLV-III has been transmitted by cocultivation with lymphocytes from AIDS (designated H9/HTLV-III$_B$) were tested with human sera in a strip radioimmunoassay (RIA) based on the Western Blot technique. The sera used for the analysis were also tested by ELISA with purified HTLV-III. Sera from patients with AIDS and from some homosexuals and heroin-addicts recognized a number of specific antigens not detected by any other means. The most prominent reactions are with antigens of about MW 41,000. In short, the antigens associated with HTLV-III virus produced by HT cells permits the detection of antibodies in AIDS and pre-AIDS patients. This virus-infected cell line also makes possible the detection of AIDS and pre-AIDS in other samples of human sera, such as donated blood.

As is indicated above, the major immune reactivity or specificity is directed against p41, a 41,000 MW protein constituting the envelope antigen of the HTLV-III virus. It is believed that additional purification and refinement of p41 might lead to an even more sensitive ELISA assay. The figure illustrates the noted specificity for p41. Although p41 appears to be the prominent antigen, sera from patients with AIDS, some homosexuals, and heroin addicts recognize a number of specific antigens not detected in normal sera. These antigens are about MW 65,000 (p65), 60,000 (p60), 55,000 (p55), and 24,000 (p24). Although other antigens were detected, these were the most significant. Example 4 illustrates the specificity of these reactions.

SPECIFIC DISCLOSURE

HTLV-III was concentrated by ultracentrifugation from virus producer culture supernatants (H9/HTLV-III$_B$) and after careful removal of lipids and cell debris by centrifugation through a cushion of 20% (W/W) sucrose in TNE buffer (10 mM Tris-NaCl, pH 7.4, 0.1 M NaCl and 0.001 mM EDTA) was purified by equilibrium density banding through a linear gradient of 20-60% sucrose (W/W) in TNE. The gradient is divided into several small fractions and the virus band located by assaying aliquots of each fraction for HTLV-III-specific reverse transcriptase activity. This produces the antigen component (HTLV-III) suitable for use in ELISA or Western Blot assay procedures.

Radioimmunoassay techniques for detecting antibodies include radiolabeled assays of the so-called blot technique, such as the Western Blot technique exemplified by Example 2, post.

Also operable and most preferred for the detection of antibodies are the enzyme-linked immunosorbent assay (ELISA) shown in Example 1.

Thirdly, antibodies to HTLV-III may be detected by an indirect immunofluorescence assay. See Example 3 for this technique. This assay is significant because it uses the infected T-cell as a starting material. ELISA and Western Blot techniques start with the HTLV-III virus.

Antibodies to HTLV-III are detected in sera of patients with AIDS and pre-AIDS lymphadenopathy syndrome by the process of the present invention. Example 1 is a detailed description of the present invention using the ELISA technique. Example 2 is a detailed description of the present invention using the Western Blot technique.

In general, the ELISA technique involves reacting a lysate of density-banded HTLV-III to the test sera, blood taken from a human patient. The mixture is then incubated with a peroxidase labeled antibody. Any wells positive for the presence of AIDS antibodies forms a detectable and measurable color product.

As indicated above, antibodies to HTLV-III may also be detected in sera of patients with AIDS or pre-AIDS by means of the Western Blot technique. HTLV-III is lysed and electrophoretically fractionated on a polyacrylamide slab gel. Protein bands on the gel are then electrophoretically transferred to a nitrocellulose sheet. Strip solid phase radioimmunoassays have been performed. Test sera obtained from human patients suspected of contraction with AIDS is then added to tubes containing the above described strips. Another antibody of $^{125}$I labeled goat anti-human immunoglobulin is added to the reaction strips which are then exposed to X-ray film. Strips positive for the presence of AIDS antibodies exhibit wide bands at the 41,000 Mr location.

EXAMPLE 1

Antibodies to HTLV-III in Sera of Patients with AIDS and pre-AIDS Lymphadenopathy Syndrome Wells of 96-well plates were coated overnight with a lysate of density-banded HTLV-III at 0.5 μg protein per well in 100 μl 50 mM sodium bicarbonate buffer, pH 9.6. The wells were washed with water and incubated for 20 min. with 100 μl of 5% bovine serum albumin in phosphate buffered saline (PBS). After washing, 100 μl of 20% normal goat serum in PBS were added to each well, followed by 5 or 10 μl of the test sera (blood taken from a human patient), and allowed to react for 2 hr. at room temperature. The wells were washed three times with 0.5% Tween-20 in PBS in order to remove unbound antibodies and incubated for 1 hr. at room temperature with peroxidase labeled goat anti-human IgG at a dilution of 1:2000 in 1% normal goat serum in PBS. Goat anti-human IgG is a second antibody that binds with the antibody antigen complex formed in positive wells. The wells were successively washed 4 times with 0.05% Tween 20 in PBS and 4 times with PBS to remove unbound goat antibody and reacted with 100 μl of the substrate mixture containing 0.05% orthophenylene diamine and 0.005% hydrogen peroxide in phosphate-citrate buffer, pH 5.0. This substrate mixture detects the peroxidase label and forms a color product. The reactions were stopped by the addition of 50 μl of 4N H$_2$SO$_4$ and the color yield measured using an ELISA reader which quantifies the color reading. Assays were performed in duplicate; absorbance readings greater than three times the average of 4 normal negative control readings were taken as positive. The results are shown in Table 1.

TABLE 1

| Subjects | No. Positive/No. Tested | Percent Positive |
|---|---|---|
| Patients with AIDS | 43/49 | 87.8 |
| Pre-AIDS | 11/14 | 78.6 |
| Intravenous Drug abusers | 3/5 | 60 |
| Homosexual men | 6/17 | |
| Sexual contact of AIDS patient | 1/1 | |
| Persistent fatigue | 1/1 | |
| Other | 4/15 | 26.6 |
| Other controls | 1/186 | 0.5 |
| Normal subjects | 1/164 | 0.6 |
| Patients with Hepatitis B virus infection | 0/3 | 0 |
| Patients with Rheumatoid arthritis | 0/1 | 0 |
| Patients with Systemic lupus erythematosus | 0/6 | 0 |
| Patients with acute mononucleosis | 0/4 | 0 |
| Patients with lymphatic leukemias | 0/8 | 0 |

EXAMPLE 2

Western Blot analysis of the test sera was conducted as follows. HTLV-III was lysed and fractionated by electrophoresis on a 12% polyacrylamide slab gel in the presence of sodium dodecylsulfate (SDS). The protein bands on the gel were electrophoretically transferred to a nitrocellulose sheet, according to the procedure of Towbin et al., *Proc. Natl. Acad. Sci. USA*, 76:4350 (1979). Strip solid phase radioimmunoassays were then performed. The sheet was incubated at 37° for 2 hr. with 5% bovine serum albumin in 10 mM Tris-HCl, pH 7.5 containing 0.9% NaCl and cut into 0.5 cm strips. Each strip was incubated for 2 hr. at 37° and 2 hr. at room temperature in a screw cap tube containing 2.5 ml of buffer 1 (20 mM Tris-HCl, pH 7.5, 1 mM EDTA, 0.2 M NaCl, 0.3% Triton X-100 and 2 mg/ml bovine serum albumin and 0.2 mg/ml of human antibody fractions, Fab). Test sera (25 $\mu$l), taken from human patients with AIDS or exhibiting pre-AIDS symptoms, were then added to individual tubes containing the strips and incubation continued for 1 hr. at room temperature and overnight in the cold. The strips were washed three times with solution containing 0.5% sodium deoxycholate, 0.1 M NaCl, 0.5% Triton X-100, 1 mM phenylmethylsulfonyl fluoride and 10 mM sodium phosphate, pH 7.5. The strips were incubated for 1 hr. at room temperature with 2.4 ml of buffer 1 and 0.1 ml of normal goat serum. Affinity purified and $^{125}$I-labeled goat anti-human immunoglobulin ($\mu$chain and Fc fragment) ($1.25 \times 10^6$ cpm) were added to the reaction mixture and the incubation continued for 30 min. at room temperature. The strips were washed as described, dried, mounted and exposed to X-ray film. FIG. 1 indicates graphically the results of these experiments. Strip 1 is test sera from an adult with T-cell leukemia; Strip 2 is a normal donor; Strip 3 is a mother of a child with AIDS; Strips 4 and 6-10 are AIDS patients; and Strip 5 is a patient with pre-AIDS.

EXAMPLE 3

Fixed Cell and Live Cell Indirect Immunofluorescence Assay for Antibodies to HTLV-III Indicator cell—HTLV-III infected negative cells; negative control—uninfected T-cells.

Infected cells were washed with phosphate buffered saline (PBS) and resuspended in PBS at $10^6$ cells/ml. Approximately 50 of cell suspension were spotted on a slide, air dried, and fixed in acetone for 10 min. at room temperature. Slides were stored at $-20°$ C. until ready for use. 20 ml of the test human serum diluted 1:10 in PBS were added to the fixed cells and incubated for 1 hr. at 37°. Slides were washed and reacted for 30 min. at room temperature with a dilute solution of fluorescein-conjugated goat anti-human IgG. Slides were again washed and examined under a microscope for fluorescence. A negative control used uninfected parental cells. The above describes a fixed cell system in which the antibody antigen reaction is sought for both inside and outside the cell.

For live cell immunofluorescence assay all the above reactions were done in a tube instead of on the slide, but without chemical fixation of the cells. After reaction with the fluorescein conjugated antihuman antibody, the cells were added to the slide and examined under a microscope for antibody-antigen reaction on the surface of the cell.

The results of each of these assays show a strong fluorescence reaction specifically with sera of AIDS and pre-AIDS patients.

EXAMPLE 4

Sera of patients with clinically documented AIDS, Kaposi's sarcoma, sexual contacts of AIDS patients, intravenous drug abusers, and homosexual men and heterosexual donors were tested for their reactivity to HTLV-III. The system employed was ELISA. Lysates of sucrose density banded HTLV-III were coated on 96-well microtiter plate wells. Test sera were diluted with a dilute solution of normal goat serum, added to the wells, and allowed to react for 2 hr. or overnight at room temperature. The antibodies in the human sera were detected by the reaction of the primary immune complex with peroxidase labeled goat anti-human immunoglobulins followed by the development of a colored peroxidase reaction product. The results obtained are presented in Table 1. Of 49 clinically diagnosed AIDS patients, 43 (88%) showed serum reactivity in this assay. Fourteen homosexual men with pre-AIDS were also tested for antibodies to HTLV-III. Of these, 11 (79%) were positive. Among 17 homosexual men with no clinical symptoms of AIDS, 7 scored positive. Of these, at least one was known to be a long-time sexual partner of a diagnosed case of AIDS. One had persistent fatigue and was exhibiting early signs of AIDS. One of the three intravenous drug abusers that were positive for serum antibodies to HTLV-III was also a homosexual.

In contrast, only 1 of 186 controls tested reacted positive in this test. They included 3 with hepatitis B virus infection, 1 with rheumatoid arthritis, 6 with systemic lupus erythematosus, 4 with acute mononucleosis and 8 with various forms of lymphatic leukemias and lymphomas, some of whom were positive for HTLV-I. The remaining test subjects were normal donors of unknown sexual preference, including laboratory workers ranging in age from 22 to 50.

EXAMPLE 5

To investigate the specificity of the reactions, lysates of the HTLV-III-infected cell clones were analyzed in comparison with lysates of the same cell clones before viral infection. No antigen was found reactive in the uninfected clones, with the exception of a MW 80,000 band in H17 which bound antibodies from all human sera tested, but not from rabbit or goat serum. Antigens newly expressed after viral infection and recognized by the human serum used for this analysis include p65, p55, p41, p39, p32, and p24. In addition, a large protein of approximately MW 130,000 and one of 48,000 were detected. With normal human serum, none of the antigens was detected. These results show that the antigens detected are either virus-coded proteins or cellular antigens specifically induced by viral infection.

EXAMPLE 6

Therapeutic AIDS specific test kits were constructed for detecting antibodies using several different techniques for detection. One test kit for antibodies detection comprised a compartmented enclosure containing a plurality of wells, plates which were coated prior to use with HTLV-III and ELISA materials for enzyme detection consisting of normal goat serum and peroxidase, labeled goat antihuman IgG and a color change indicator consisting of orthophenylene diamine and hydrogen peroxide in phosphate citrate buffer.

A second test kit for detecting antibodies using the Western Blot technique comprised a container, a cover, and therein containing a nitrocellulose sheet and a polyacrylamide slab gel in the presence of sodium dodecylsulfate, and additionally surfactants as well as pH modifiers and bovine serum albumin and human Fab, and additionally this Western Blot analysis container also contained a supply of dilute normal goat serum and $I^{125}$ labeled goat antihuman immunoglobulin and a source of HTLV.

Finally, a different AIDS specific test kit for detecting antibodies using the indirect immunofluorescence assay comprised a compartmental container, human test serum containing HTLV-III, phosphate buffered saline, and fluorescein-conjugated goat antiserum IgG.

We claim:

1. A method for the detection of antibodies which specifically bind to antigenic sites of the Human T-cell Leukemia Virus-III (HTLV-III) virion in samples of the body fluids of patients with Acquired Immune Deficiency Syndrome (AIDS) or risk of AIDS (pre-AIDS) which comprises contacting HTLV-III or fractions thereof said sample with antibodies from human sera taken from AIDS patients and measuring the formation of antigen-antibody complexes by strip radioimmunoassay based on Western Blot technique or ELISA (an enzyme-linked immunosorbent assay) or indirect immunofluorescent assay.

2. The method according to claim 1 wherein the HTLV-III is used in the presence of HT neoplastic aneuploid T-cells.

3. The method according to claim 1 wherein a 41,000 m.w. fraction of HTLV-III is utilized.

4. A method of testing for antibodies to HTLV-III in AIDS and pre-AIDS in sera of human patients according to claim 1 wherein said patients are specially selected being in the pre-AIDS stage or initial stage of the illness.

5. The method according to claim 1 wherein the method of measuring the formation of antigen-antibody complexes is ELISA.

6. The method of claim 5 wherein HTLV-III was concentrated by ultracentrifugation from virus culture supernatants; lipids were removed by centrifugation through 20% (W/W) sucrose in TNE buffer and the resulting gradient was divided into fractions and virus bands were located by assaying aliquots of each fraction for HTLV-III-specific reverse transcriptase activity.

7. A diagnostic test kit for detection of AIDS specific antibodies comprising a compartmented enclosure containing multiwell plates which are coated with HTLV-III and ELISA materials for enzyme detection consisting of normal goat serum and peroxidase, labeled goat antihuman IgG and a color change indicator consisting of orthophenylene diamine and hydrogen peroxide in phosphate citrate buffer.

8. The kit according to claim 7 wherein the HTLV-III is present in the form of a lysate of the virions.

9. A diagnostic AIDS specific test kit for detecting AIDS specific antibodies using the Western Blot technique comprising a container, a cover, and therein containing a nitrocellulose sheet and a polyacrylamide slab gel and sodium dodecylsulfate, and additionally surfactants as well as pH modifiers and bovine serum albumin and the Fab fragment of normal human IgG, and Western Blot analysis container which contains a supply of dilute normal goat serum and $I^{125}$ labeled goat antihuman immonoglobulin and a source of HTLV-III.

10. An AIDS specific test kit for detecting antibodies using the indirect immunofluorescence assay comprising a compartmental container, human test serum containing HTLV-III, phosphate buffered saline, and fluorescein-conjugated goat antiserum IgG.

* * * * *

UNITED STATES PATENT OFFICE
CERTIFICATE OF CORRECTION

Patent No. 4,520,113               Dated      May 28, 1985

Inventor(s) Robert C. Gallo, et al.

It is certified that error appears in the above-identified patent and that said Letters Patent are hereby corrected as shown below:

Claim 1, line 7, "said sample" should be deleted.

Signed and Sealed this

Twenty-fifth Day of February 1986

[SEAL]

Attest:

DONALD J. QUIGG

Attesting Officer        Commissioner of Patents and Trademarks